(12) United States Patent
Mori et al.

(10) Patent No.: US 6,565,531 B1
(45) Date of Patent: May 20, 2003

(54) DRUG SOLUTION DELIVERY DEVICE

(75) Inventors: Takeshi Mori, Osaka (JP); Katsuhiro Hiejima, Osaka (JP); Kazuhiko Nishiyama, Osaka (JP)

(73) Assignee: Nipro Corporation, Osaka (JP)

( * ) Notice: Subject to any disclaimer, the term of this patent is extended or adjusted under 35 U.S.C. 154(b) by 310 days.

(21) Appl. No.: 09/666,591

(22) Filed: Sep. 20, 2000

(30) Foreign Application Priority Data

Sep. 20, 1999 (JP) .......................... 11-265650

(51) Int. Cl.⁷ .............................. A61M 5/20
(52) U.S. Cl. ................. 604/135; 604/181; 604/207
(58) Field of Search .................... 604/48, 27, 131, 604/63, 134, 135, 181, 186, 187, 207, 208, 211, 218, 221, 228, 245, 246

(56) References Cited

U.S. PATENT DOCUMENTS

| | | | | |
|---|---|---|---|---|
| 2,183,482 A | * | 12/1939 | Kurkjian | 604/135 |
| 2,605,765 A | * | 8/1952 | Kollsman | 604/135 |
| 3,214,067 A | * | 10/1965 | Linington | 222/341 |
| 4,735,611 A | * | 4/1988 | Anderson et al. | 604/130 |
| 4,966,585 A | * | 10/1990 | Gangemi | 604/131 |
| 4,991,742 A | * | 2/1991 | Chang | 222/95 |
| 4,997,420 A | * | 3/1991 | LeFevre | 604/121 |
| 5,100,389 A | * | 3/1992 | Vaillancourt | 604/135 |
| 5,140,862 A | | 8/1992 | Pappalardo | |
| 5,178,609 A | * | 1/1993 | Ishikawa | 604/131 |
| 5,389,075 A | * | 2/1995 | Vladimirsky | 604/110 |
| 5,976,112 A | * | 11/1999 | Lyza, Jr. | 604/199 |
| 6,019,747 A | * | 2/2000 | McPhee | 604/211 |
| 6,083,201 A | * | 7/2000 | Skinkle | 604/151 |

FOREIGN PATENT DOCUMENTS

| | | |
|---|---|---|
| JP | 42360 | 1/1992 |
| JP | 7509 | 1/1995 |

* cited by examiner

*Primary Examiner*—Brian L. Casler
*Assistant Examiner*—Jennifer Maynard
(74) *Attorney, Agent, or Firm*—Birch, Stewart, Kolasch & Birch, LLP

(57) ABSTRACT

A drug solution delivery device comprises barrel (1) provided with a port at a distal end thereof and opened at a proximal end thereof, gasket (2) fluid-tightly and slidably arranged in the barrel, cylindrical connecting member (3) having proximal end (32) and distal end (31) to which gasket (2) is releasably connected, plunger (4) removably connected to proximal end (32) of connecting member (3), and pressed helical spring (5) arranged between gasket (2) and connecting member (3).

19 Claims, 11 Drawing Sheets

DRUG SOLUTION DELIVERY DEVICE

BACKGROUND OF THE INVENTION

The present invention relates to a drug solution delivery device and, more particularly, a spring-loaded delivery device for delivering a drug solution into a blood vessel, extradural cavity, subcutaneous tissue, or bladder of a patient by a restoring force of a spring.

Up to now, there have been used various types of drug delivery devices as means for delivering a drug solution such as an antibiotic agent, anticancer agent or the like into a blood vessel or extradural cavity of a patient by little and little. For example, Japanese patent unexamined publication JP-A 4-2360 discloses a drug solution delivery device utilizing a contractile force of a balloon made of an elastomeric material to deliver the drug solution into a blood vessel over a relatively long period of time. The delivery device comprises a balloon having a multi-layered tubular structure made of a natural rubber and covered with an inner layer of silicone resin, a housing for holding the balloon, and flow control means for controlling a flow rate of the drug solution to be delivered to the patient. Thus, the balloon in this device serves as a container for storing a drug solution and also as a power source for delivering the drug solution.

In the device utilizing the contractile force of the balloon, however, it is inevitable for the balloon to be affected by the material used. That is, the pressure for delivery of the drug solution varies with time because of the elastomeric material used for the balloon, thus making it impossible to perform delivery of the drug solution at an accurately controlled flow rate or quantity. In addition, it is required to select an elastomeric material free from elution of ingredients as the balloon is used for storing a drug solution therein.

To solve these problems, it has been proposed to provide a delivery device of a syringe type employing an elastic member such as a helical coil spring, constant-load spring or elastic cords as means for driving the plunger, for example, in Japanese patent unexamined publication JP-A 7-509.

However, it is required to protect the device with a capsule to avoid the plunger from being accidentally pushed by hand because of the fact that the device is so designed as to push the plunger by the elastic member. Thus, the device becomes large in size and is inadequate for use in a portable form.

BRIEF SUMMARY OF THE INVENTION

The present invention has been made under these circumstances and has aimed at providing a drug solution delivery device which makes it possible to fill the device with a drug solution directly from a vial as well as to observe a residual quantity of the drug solution accurately during delivery.

The present invention has been achieved on the basis of the finding that the device can be miniaturized by directly driving a gasket with driving means.

According to the present invention, there is provided a drug solution delivery device comprising: a barrel provided at a distal end thereof with a port and opened at a proximal end thereof; a gasket fluid-tightly and slidably arranged in a lumen of the barrel; a cylindrical connecting member having a proximal end and a distal end to which said gasket is being releasably connected; a plunger removably engaged with the proximal end of said connecting member; and a helical spring pressed and arranged between said gasket and said connecting member to push the gasket by a restoring force thereof to deliver a drug solution.

In case that the spring is to be pressed and arranged between the gasket and the connecting member, the connecting member may be formed into a stepped hollow cylindrical member comprising a small-sized distal portion having an external diameter smaller than an internal diameter of the barrel. In this case, the spring may be arranged so as to surround the small-sized distal portion of the connecting member. Alternatively, the gasket may be provided with a hook having an elongated shank so that the helical spring may be arranged so as to surround the shank of the hook.

In case that the distal portion of the connecting member is formed into a cylindrical form having an external diameter smaller than the internal diameter of the barrel, the spring may be mounted on the connecting member so as to surround the small-sized distal portion. In this case, the connection between the gasket and the connecting member may be released by rotating the connecting member around an axis thereof.

Further, the gasket may be connected to the connecting member by providing at least one elongated flexible hook at a proximal end thereof and removably inserting it into a circular connecting hole formed in a closure wall of a connecting member. In this case, the gasket is released from the connecting member by bending the hooks inwardly.

When employing a gasket provided at a proximal end thereof with one or more hooks having an elongated shank portion, the helical spring may be mounted on the gasket so as to surround the shank portion of the hooks. In this case, the connecting member may be provided at a distal end thereof with a closure wall having a connecting hole on an axis thereof so that the hooks of the gasket are rotatably inserted into and removably engaged with the connecting hole. The connection between the gasket and the connecting member may be released by rotating the connecting member around an axis thereof. Alternatively, the connecting member may be provided with a circular connecting hole in a distal closed-end wall thereof, while employing the gasket provided with at lease one elongated flexible hook. In this case, the connection between the gasket and the connecting member may be released by bending the hook inwardly.

The connecting member may be provided at a distal end thereof with one or two crossbars, which cross the lumen of the connecting member, for engagement with the hook, so that the connection between the gasket and the connecting member is released by turning the connecting member around an axis thereof. In this case, the connecting member may be provided at a distal portion thereof with a small-sized cylindrical portion having an external diameter smaller than the internal diameter of the barrel, and the hook is arranged in the lumen of the small-sized cylindrical portion along with a helical spring surrounding a shank of the hook.

It is preferred to disengage the plunger from the proximal end of the connecting member by rotating the plunger about an axis thereof. However, the disengagement between the plunger and connecting member is not limited to the above means. Further, it is preferred to provide plural longitudinal ribs on the inner surface of the barrel and the outer surface of the gasket in order to prevent the gasket from being rotated around an axis thereof when rotating the plunger or the connecting member. In this case, the ribs of the gasket are engaged with the ribs of the barrel so that the gasket is prevented from being rotated around an axis thereof when rotating the plunger or connecting member.

Further scope of applicability of the present invention will become apparent form the detailed description given hereinafter. However, it should be understood that the detailed description and specific example, while indicating preferred embodiments of the invention, are given by way of illustration only. Various changes and modifications within the spirit and scope of the invention will become apparent to those skilled in the art form the detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
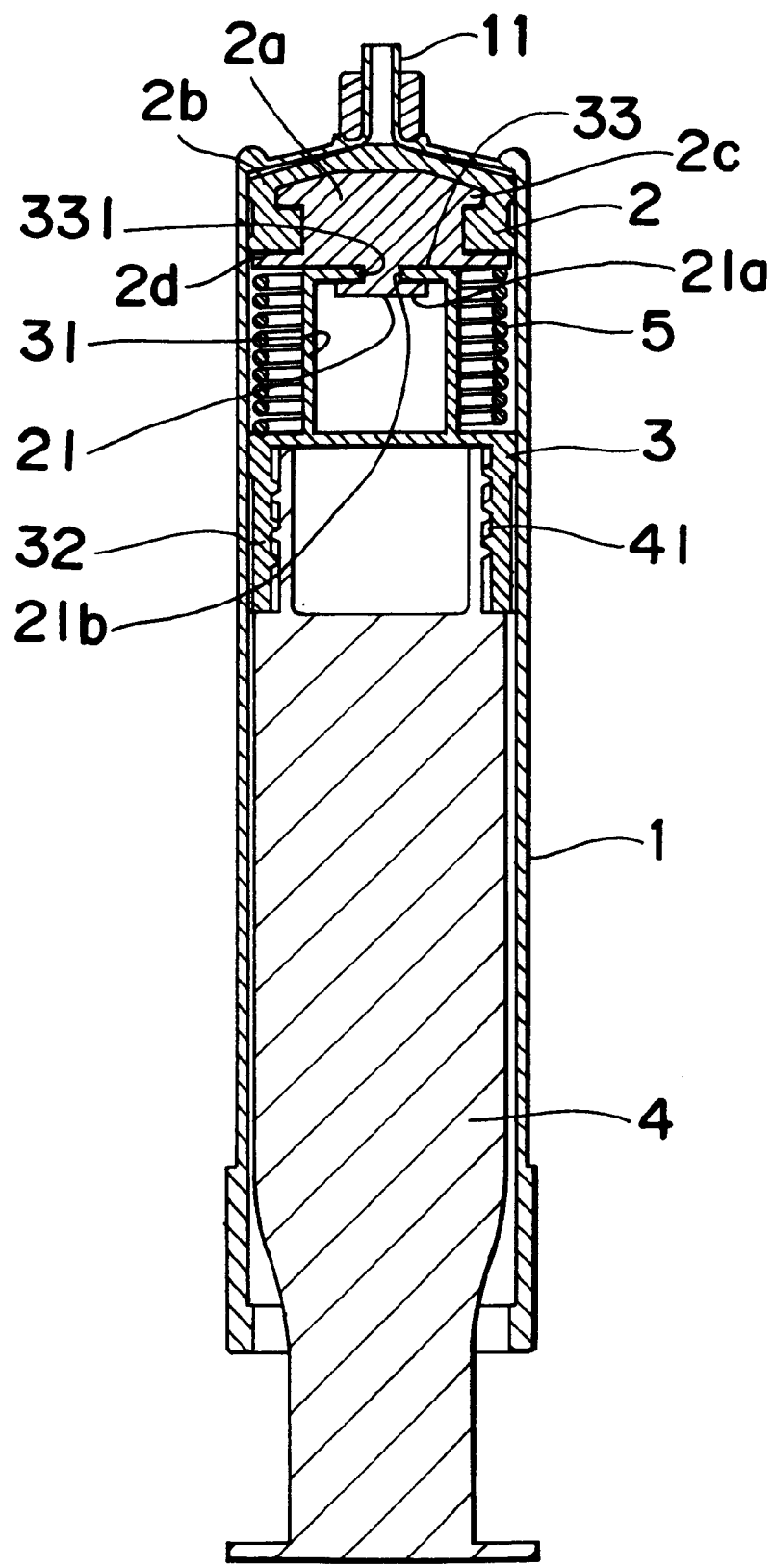
FIG. 1 is a longitudinal sectional view of a drug solution delivery device illustrating one embodiment of the present invention.

As illustrated in FIGS. 1 to 8, a drug solution delivery device according to the present invention comprises a barrel 1, a gasket 2, a connecting member 3, a plunger 4 and a helical spring 5. The barrel 1 is a hollow cylindrical member opened at a proximal end and provided with aport portion 11 at a distal end. The gasket 2 comprises a solid core member 2a and a sealing member 2b made of an elastomeric sealing material and fitted on the core member 2a. The gasket 2 is liquid-tightly and slidably arranged in a lumen of the barrel 1. The core member 2a is provided with a head portion 2c at a distal end and an outwardly extended flange portion 2d at a proximal end thereof.

The connecting member 3 is a stepped cylindrical member having a distal portion 31 and a proximal portion 32. The gasket 2 is releasably connected to the distal portion 31 by connecting means mentioned below, while the plunger 4 being removably engaged with the proximal portion 32. A helical spring 5 is compressed and arranged between gasket 1 and plunger 4. When the gasket 2 is released from the connecting member 3, the gasket 2 is pushed toward the distal end of the barrel 1 by the restoring force of the helical spring 5, and a drug solution is delivered from the barrel 1.

The distal portion 31 of the connecting member 3 of the devices shown in FIGS. 1 to 4 is formed into a cylindrical shape having an external diameter smaller than the internal diameter of the barrel 1, so that a cylindrical space is formed between them. Thus, the helical spring 5 is fitted around the small-sized cylindrical distal portion 31 and accommodated in the cylindrical space surrounded by a distal portion of connecting member 3, internal surface of the barrel 1 and gasket 3. Preferably, the connection between the proximal portion 32 of the connecting member 3 and the plunger is performed by screw engagement. In this case, the connecting portion 41 of the plunger 4 is preferably formed into a positive pattern as a male screw.

In the embodiment of FIG. 1, the connecting member 3 is closed at a distal end thereof with a closure wall 33. This closure wall 33 is provided with connecting means such as, for example, a connecting hole 331 for attachment of connection means such as, for example, a hook 21 of the gasket 2. In this case, the gasket 2 is released from the connecting member 3 by rotating the connecting member 3 around an axis thereof. Specifically, for example, the connecting member 3 may take a configuration as illustrated in FIG. 10.

Figure 10:
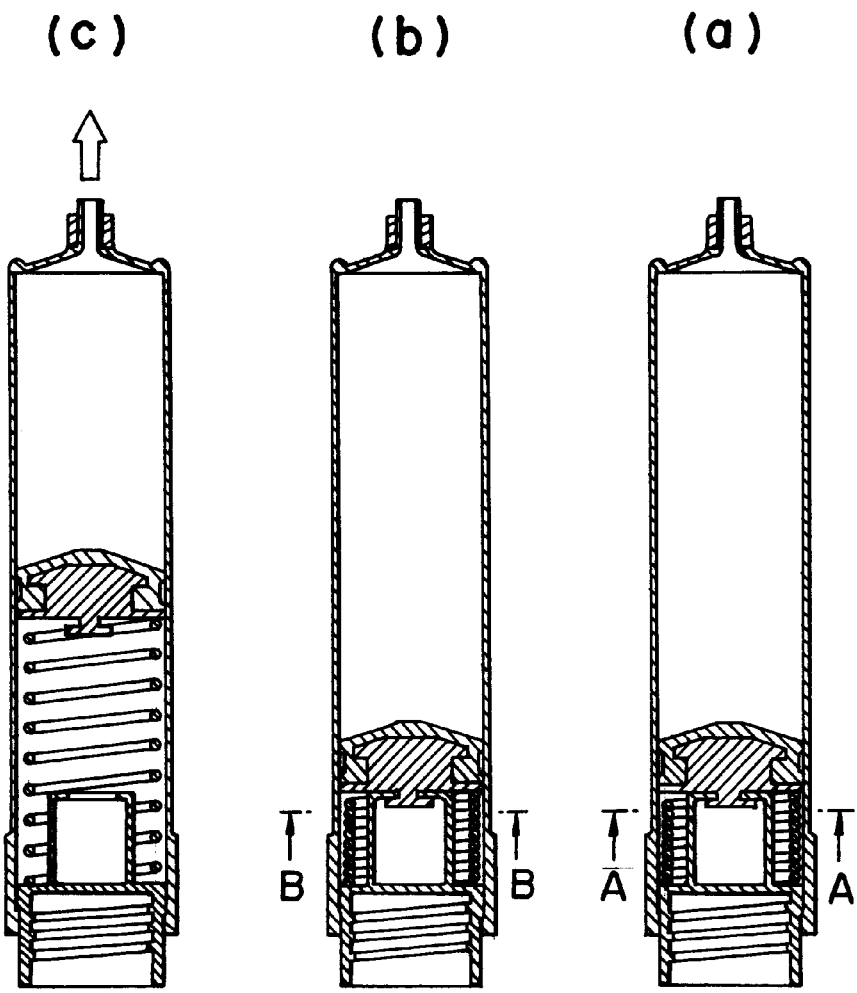
FIG. 10 is a schematic diagram of the delivery device of FIG. 1, illustrating steps of delivering the drug solution from the device.
Figure 10:
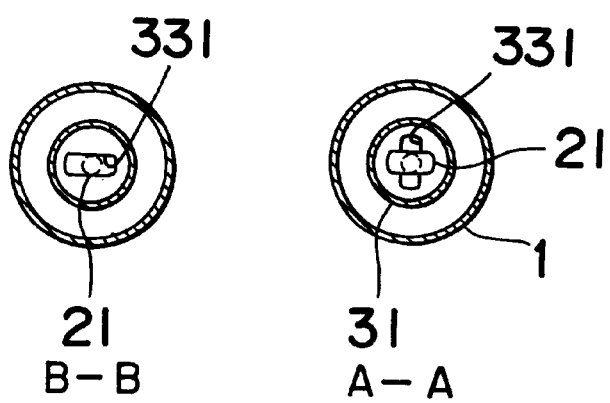

In this embodiment, the connecting hole 331 is formed into a rectangular shape (in plan) as illustrated in the cross-sectional view of FIG. 10. The core 2b of the gasket 2 is provided as an integral part thereof with a hook 21. When taking a side view, the hook 21 has T-shaped configuration including a head portion 21a and a cylindrical shank portion 21b, as illustrated in the longitudinal section. The head portion 21a is formed into a similar rectangular figure slightly smaller than the size of the connecting hole 331, while the shank portion 21b is formed into a cylindrical form having a diameter smaller than a size of the short side of rectangular hole 331. Thus, the head portion 21a of the hook 21 may be inserted into or pulled out of the rectangular hole 331 and the shank portion may be rotatable in the connecting hole 331. The hook 21 is inserted into the connecting hole 331 and hooked to the closure wall 33 as shown in the sectional view taken along the line A—A. Thus, the hook 21 can be released from the connecting hole 331 by turning the connecting member 3 around an axis thereof until the connecting hole is brought into line with the direction of head portion of the hook 21 as shown in sectional view taken along the line B—B.

Figure 2:
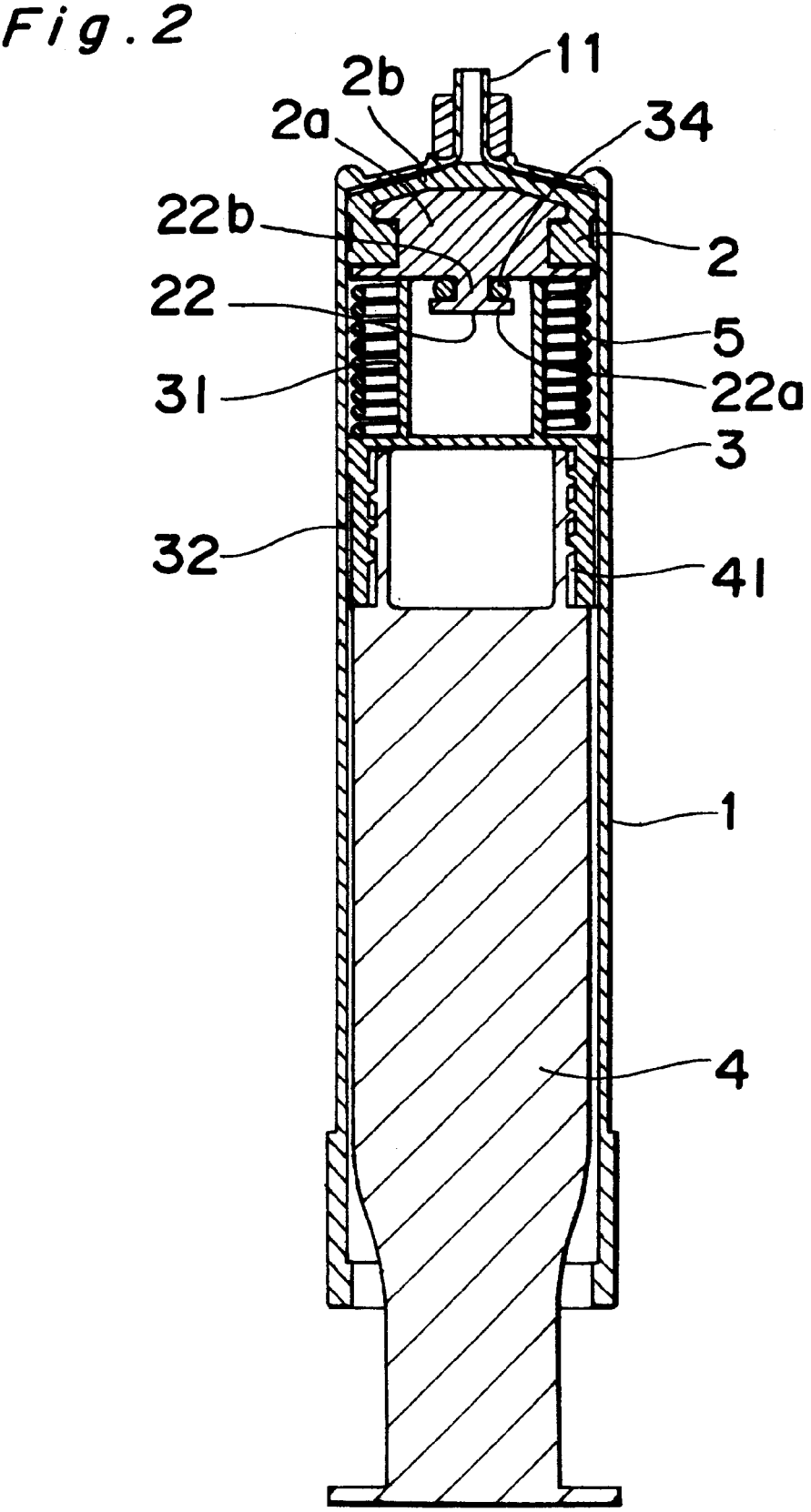
FIG. 2 is a longitudinal sectional view of a drug solution delivery device illustrating another embodiment of the present invention.

In the embodiment of FIG. 2, the connecting member 3 is provided at a distal end thereof with a pair of parallel crossbars 34, which are symmetrical about an axis of the lumen of the cylindrical distal portion 31, to form a gap between them. A hook 22 is inserted into and rotatably arranged in the gap so as to be released from the connecting member 3 by rotating the connecting member 3 around an axis thereof. The hook 22 includes a head portion 22a and a shank portion 22b. The head portion 22a is so designed as to have a width smaller than the distance between the crossbars 34 but to have a length greater than the distance between the crossbars 34. The shank portion 22b is formed, for example, into a cylindrical shape with a diameter smaller than the distance between two crossbars 34.

In this embodiment, the hook 22 is slipped from the gap between crossbars 34 by turning the connecting member 3 around an axis thereof to bring its crossbars into line with the direction of head portion of the hook 22. The connecting member 3 may be provided with one or two crossbars 34 at its small-sized distal portion 31. As illustrated in FIG. 2, however, it is preferred to provide the connecting member 3 with a pair of crossbars 34 in parallel and symmetrically about the longitudinal axis of the connecting member 3.

Figure 3:
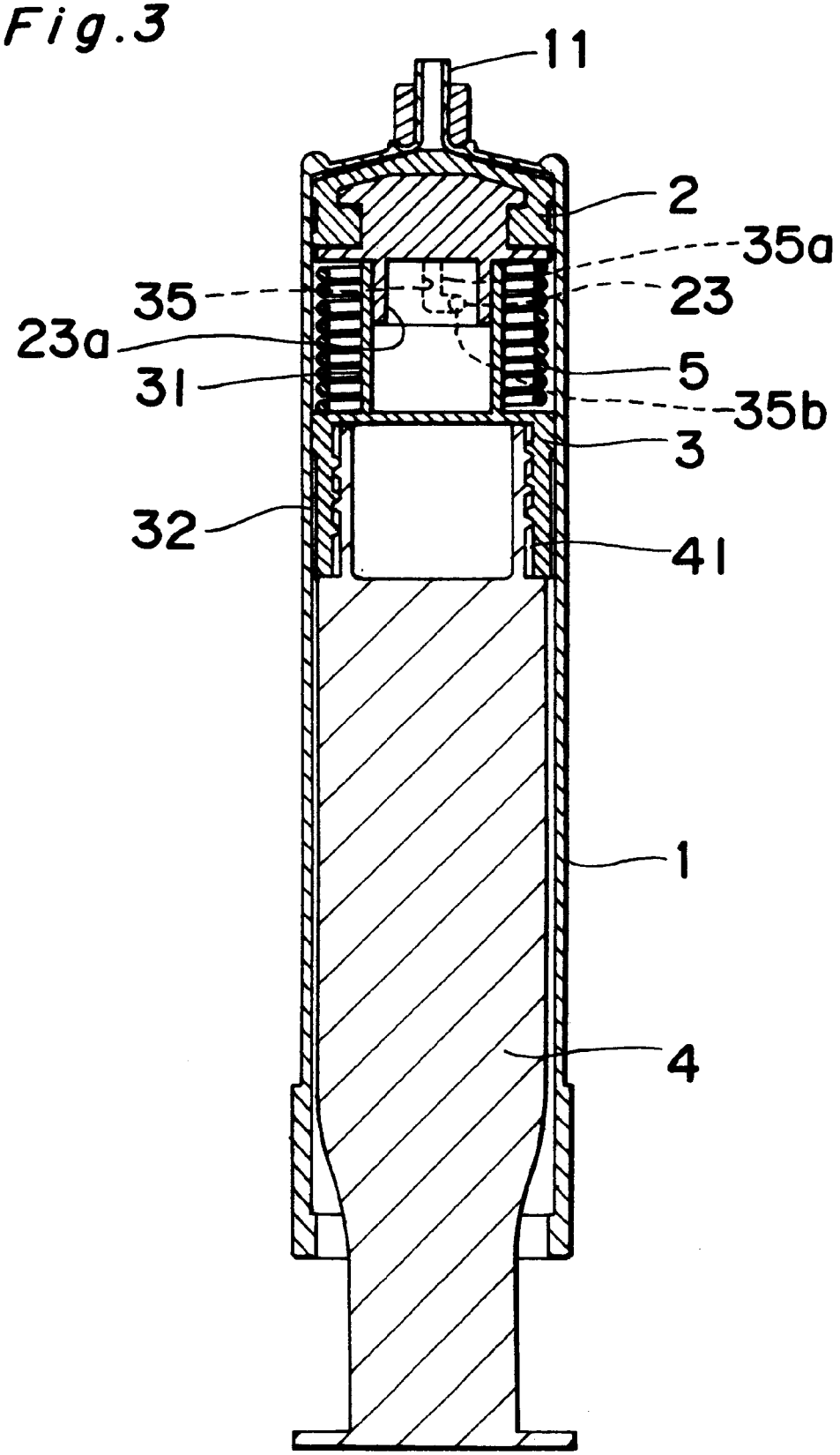
FIG. 3 is a longitudinal sectional view of a drug solution delivery device illustrating another embodiment of the present invention.

In the embodiment of FIG. 3, the delivery device has a construction similar to that of the delivery device shown in FIG. 1 except connection between connecting member 3 and gasket 2. The connecting member 3 is a stepped cylindrical member including a small-sized distal portion 31 with a distal open end. A cylindrical sidewall of the distal portion 31 is provided with an L-shaped slit 35 including an axial slit portion 35*a* and circumferential slit portion 35*b*. The axial slit portion 35*a* extends from the open end of the distal portion 31 toward the proximal end thereof in parallel with the central axis of the connecting member 3, and terminates at the circumferential slit portion 35*b*. The solid core member 2*a* of gasket 2 is provided as an integral part thereof with a cylindrical portion 23*a* having an external diameter slightly smaller than the internal diameter of the distal portion of the connecting member 3. The cylindrical portion 23*a* is provided at its outside with means for engagement with the gasket such as, for example, one or more projections 23. Each projection is inserted in the L-shaped slit 35 and engaged with its circumferential slit 35*b*. In this embodiment, the gasket 2 is released from the connecting member 3 by rotating the connecting member 3 around an axis thereof to disengage the projection 23 from the circumferential slit 35*b*. The connecting member 3 may be provided with one or more L-shaped slits 35, but it is preferred to provide a pair of L-shaped slits 35.

Figure 4:
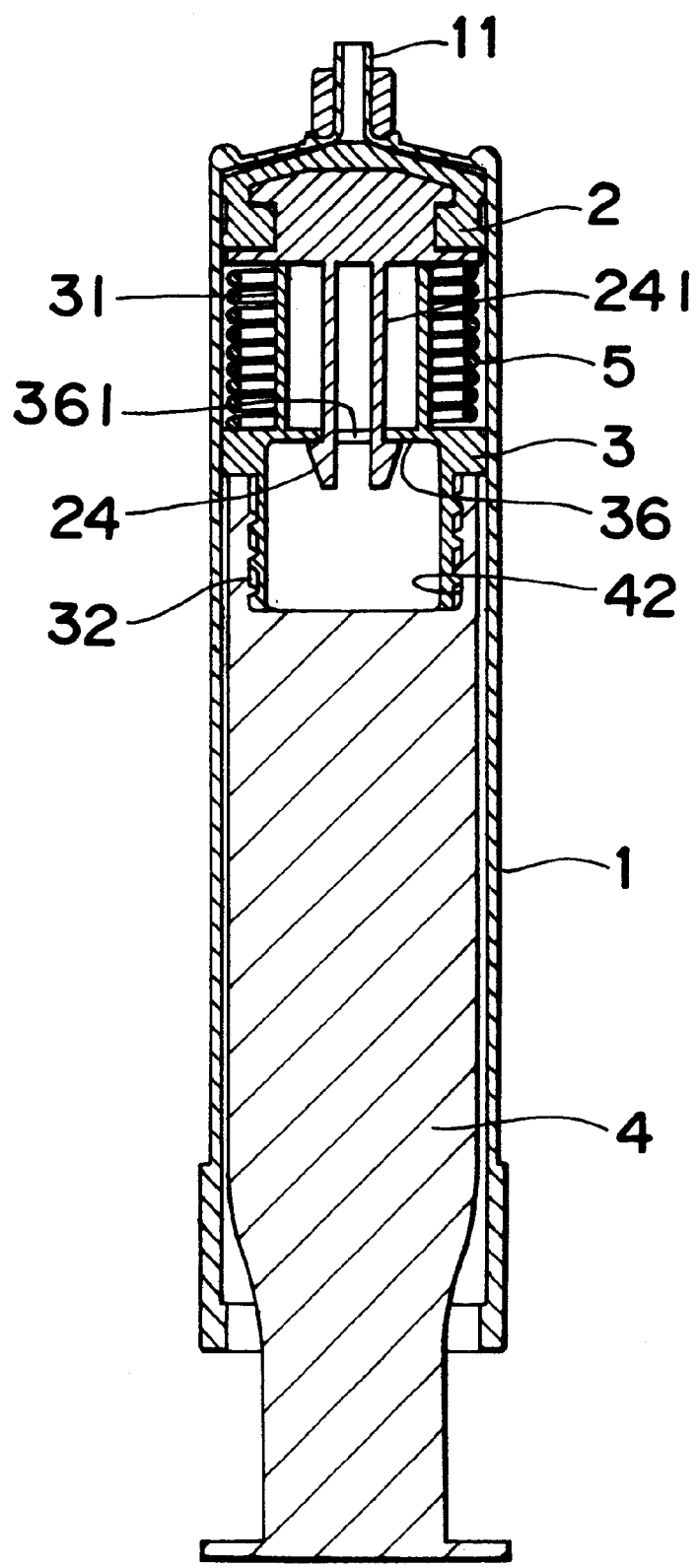
FIG. 4 is a longitudinal sectional view of a drug solution delivery device illustrating another embodiment of the present invention.

In the embodiment of FIG. 4, the connecting member 3 includes a small-sized cylindrical portion 32 closed at a proximal end thereof or stepped portion by a closure wall 36. The closure wall 36 is provided on its central axis with engaging means such as, for example, circular hole 361 for connection of the connecting member 3 with the gasket 2.

On the other hand, the gasket 2 in the embodiment of FIG. 4 is provided with engaging means such as, for example, a pair of flexible hooks 24 for engagement with the connecting member 3. Each hook 24 is composed of an elongated shank portion and an outwardly extended head portion. The head portion of the hook is inserted into the circular hole 361 of the closure wall 36 and engaged therewith at the head portions. In use, the gasket 2 can be released from the connecting member 3 by inwardly bending the hooks 24 manually to disengage the hooks 24 from the hole 361. Although the gasket 2 may be provided with one or more hooks 24, it is preferred to provide the gasket 2 with a pair of hooks 24 as illustrated in the drawing.

Figure 5:
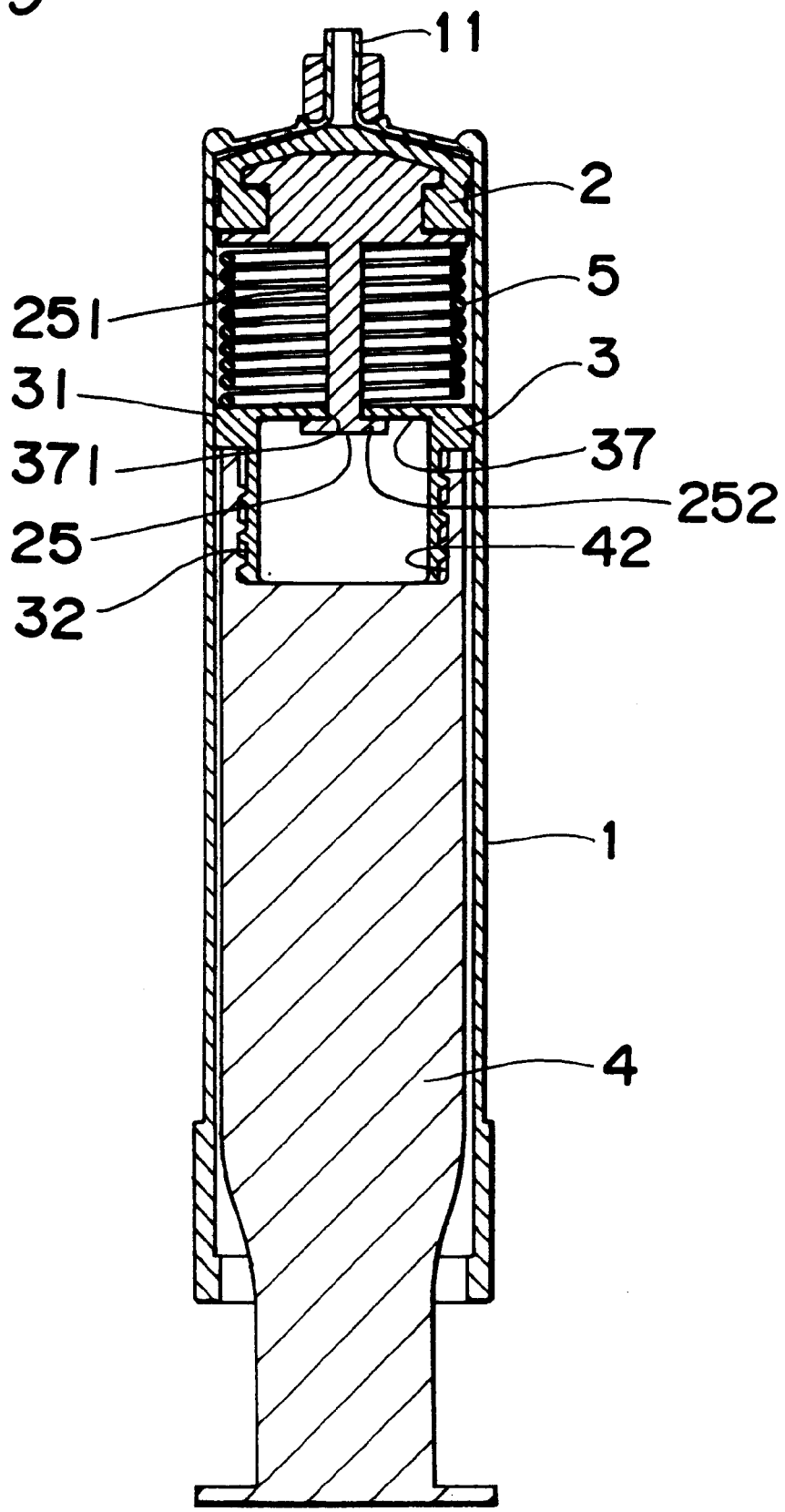
FIG. 5 is a longitudinal sectional view of a drug solution delivery device illustrating another embodiment of the present invention.
Figure 6:
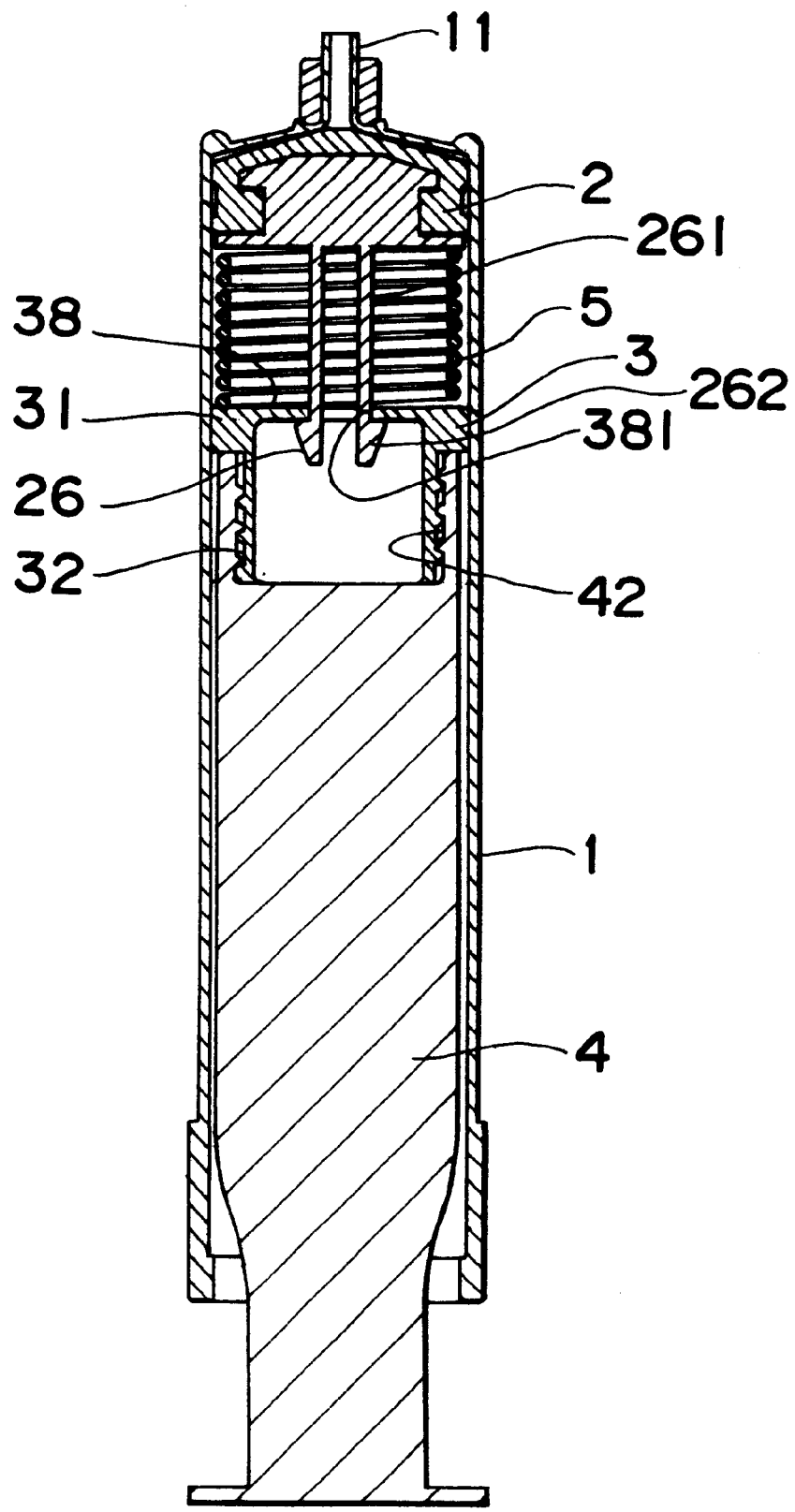
FIG. 6 is a longitudinal sectional view of a drug solution delivery device illustrating another embodiment of the present invention.
Figure 7:
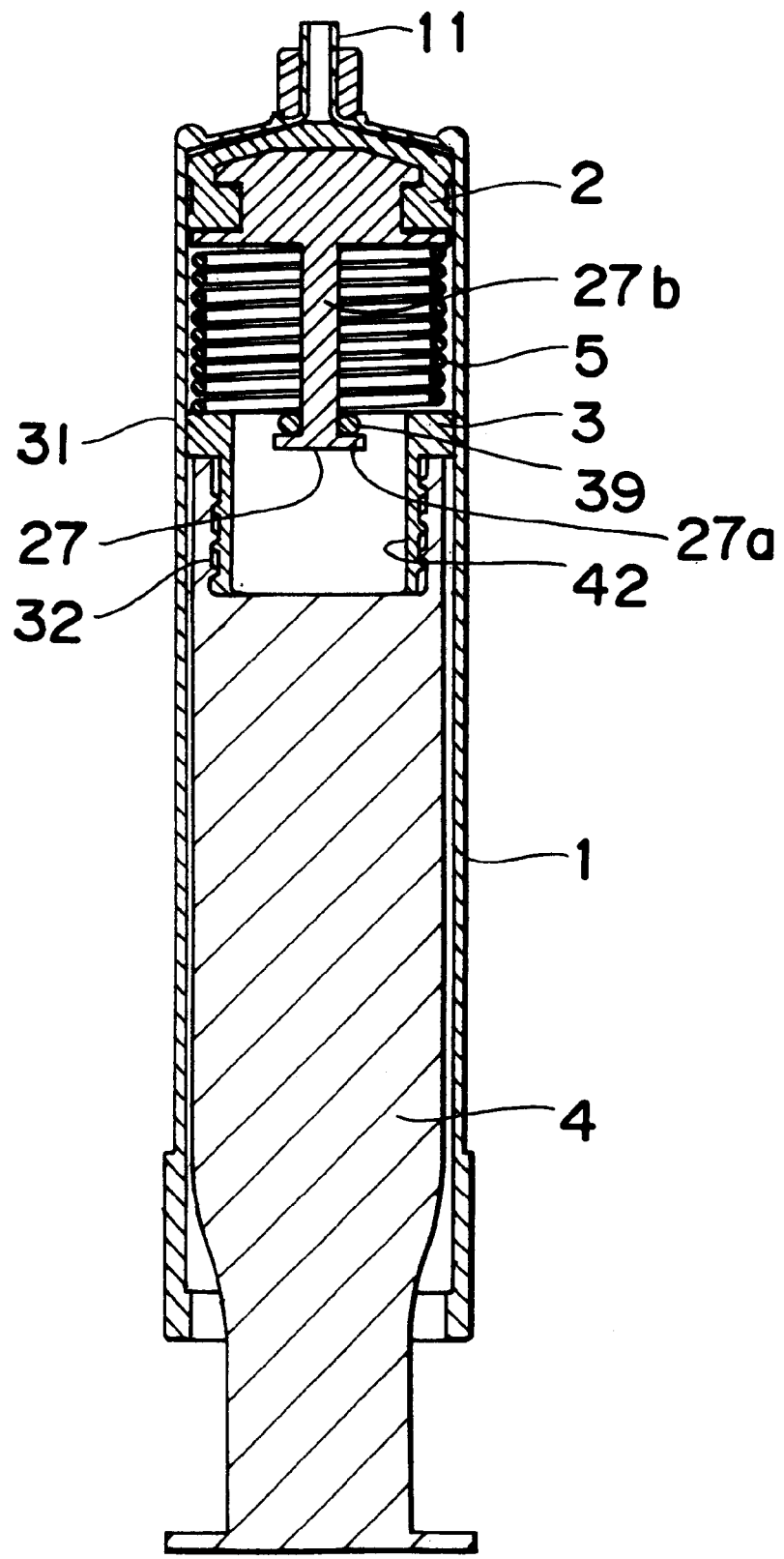
FIG. 7 is a longitudinal sectional view of a drug solution delivery device illustrating another embodiment of the present invention.

Each delivery device illustrated in FIGS. 5–7 comprises a gasket 2 provided with an elongated hook, and a helical spring 5. The spring 5 is arranged under pressed conditions in a space surrounded by the distal portion 31 of connecting member 3, gasket 2 and barrel 1, so as to surround the shank portion of the hooks 25. Preferably, the connection between proximal portion 32 of the connecting member 3 and plunger 4 is carried out by screw connection. In case of the screw connection, it is preferred to provide the plunger 4 with engaging means 42 of a female type.

The delivery device illustrated in FIG. 5 comprises a cylindrical connecting member 3 closed at a distal end thereof by a closure wall 37, and a gasket 2 including a core member 2*b* with engaging means. The closure wall 37 is provided with a rectangular connecting hole 371 for connection to the engaging means of the gasket 2, for example, a T-shaped hook 25. The hook 25 includes an elongated shank portion 251 such as, for example, a columnar shank portion having a diameter smaller than the size of short side of the rectangular hole 371, and a head portion 252 similar in shape but slightly smaller than the rectangular hole 371 in size. Thus, the head portion 252 of the hook 25 is insertable into the hole 371, while the shank portion 252 is rotatable within the hole. The hook 25 is inserted into the hole 371 and engaged at its head portion with the hole 371. Thus, the hook 25 can be released from the hole 371 by turning the connecting member 3 around an axis thereof so that the hole 371 is oriented towards the direction of the head portion 252.

The delivery device illustrated in FIG. 6 is similar to that of FIG. 4 except for construction of a connecting member 3. The connecting member 3 is a hollow cylindrical member closed at a distal end thereof by a closure wall 38. The closure wall 38 is formed as an integral part of the connecting member 3 and provided on an axis thereof with a circular connecting hole 381 for connection to engaging means, for example, a pair of hooks 26 of the gasket 2. Each hook 26 is composed of an elongated flexible shank portion 261 and a wedge-shaped head portion 262. The gasket 2 can be released from the connecting member 3 by inwardly bending the hooks 24 manually. Although the gasket 2 may be provided with one or two hooks 26, Preferably, the gasket 2 is provided with a pair of hooks 26 symmetrically about the axis as illustrated in the drawing.

An delivery device illustrated in FIG. 7 comprises a cylindrical connecting member 3 provided at a distal end thereof with a pair of parallel crossbars 39, which are symmetrical about the axis of the connecting member 3 to form a gap between them. A hook 27 is rotatably engaged with the crossbars 39 through the gap between them. Thus, the gasket 2 can be released from the connecting member 3 by turning the connecting member 3 around an axis thereof to orient it to the direction of the gap between two crossbars 39.

To this end, the hook 27 is formed into a T-shape composed of a head portion 27*a* and an elongated shank portion 27*b* extended from the proximal end of the gasket core 2*b* and terminated at the head portion 27*a*. The head portion 27*a* is so designed as to have a width smaller than the distance between the crossbars 39 and a length greater than the distance between the crossbars 39. The shank portion 27*b* is so designed as to have a diameter smaller than the distance between two crossbars 39.

In this embodiment, the hook 27 is disengaged from the crossbars 39 by turning the connecting member 3 around an axis thereof to bring its crossbars 39 into line with the direction of head portion 27*a* of the hook 27. The connecting member 3 may be provided with one or two crossbars 39 at a distal end thereof. As illustrated in the drawing, however, it is preferred to provide the connecting member 3 with a pair of crossbars 39 in parallel and symmetrically about the axis.

Figure 8:
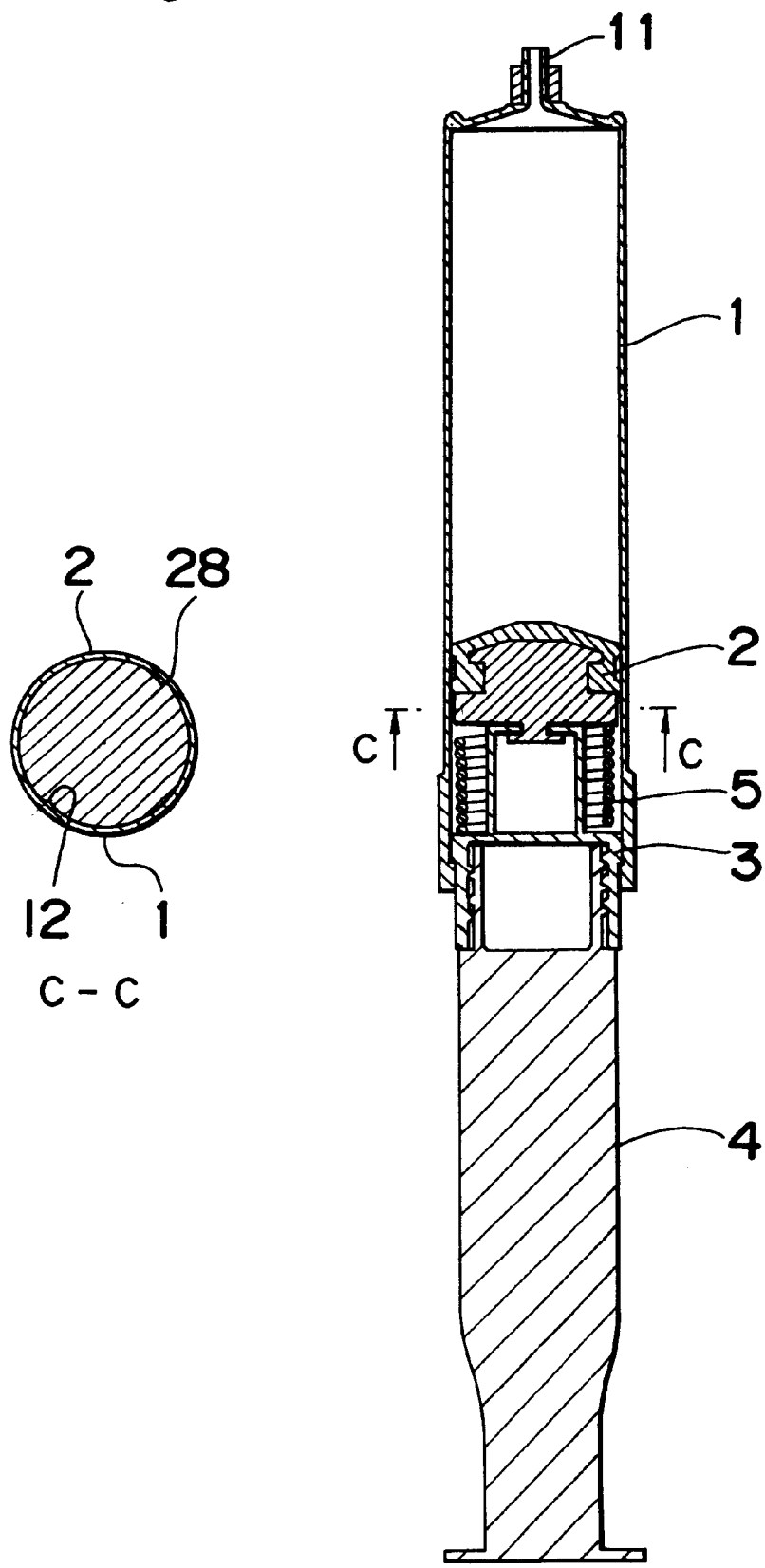
FIG. 8 is a longitudinal sectional view of a drug solution delivery device illustrating another embodiment of the present invention.

Referring now to FIG. 8, a drug solution delivery devices of this embodiment has a construction similar to that of FIG. 2 except for provision of plural longitudinal ribs 12 and 28 for preventing the gasket 2 from being rotated around the axis when turning the connecting member 3. The barrel 1 is provided with plural longitudinal ribs 12 at its internal surface, the gasket 2 is provided with ribs 28 at an external surface of a core portion, as shown in cross-section of FIG. 8. When turning the connecting member 3 around an axis thereof, the ribs 28 of the gasket 2 are engaged with the ribs 12 of the barrel 1, so that the gasket 2 is prevented from being rotated along with the connecting member 3. This makes it possible to release the gasket 2 from the connecting member 3. The provision of ribs 12 and 28 may be applied to any of other embodiments illustrated in FIGS. 2–7.

Figure 9:
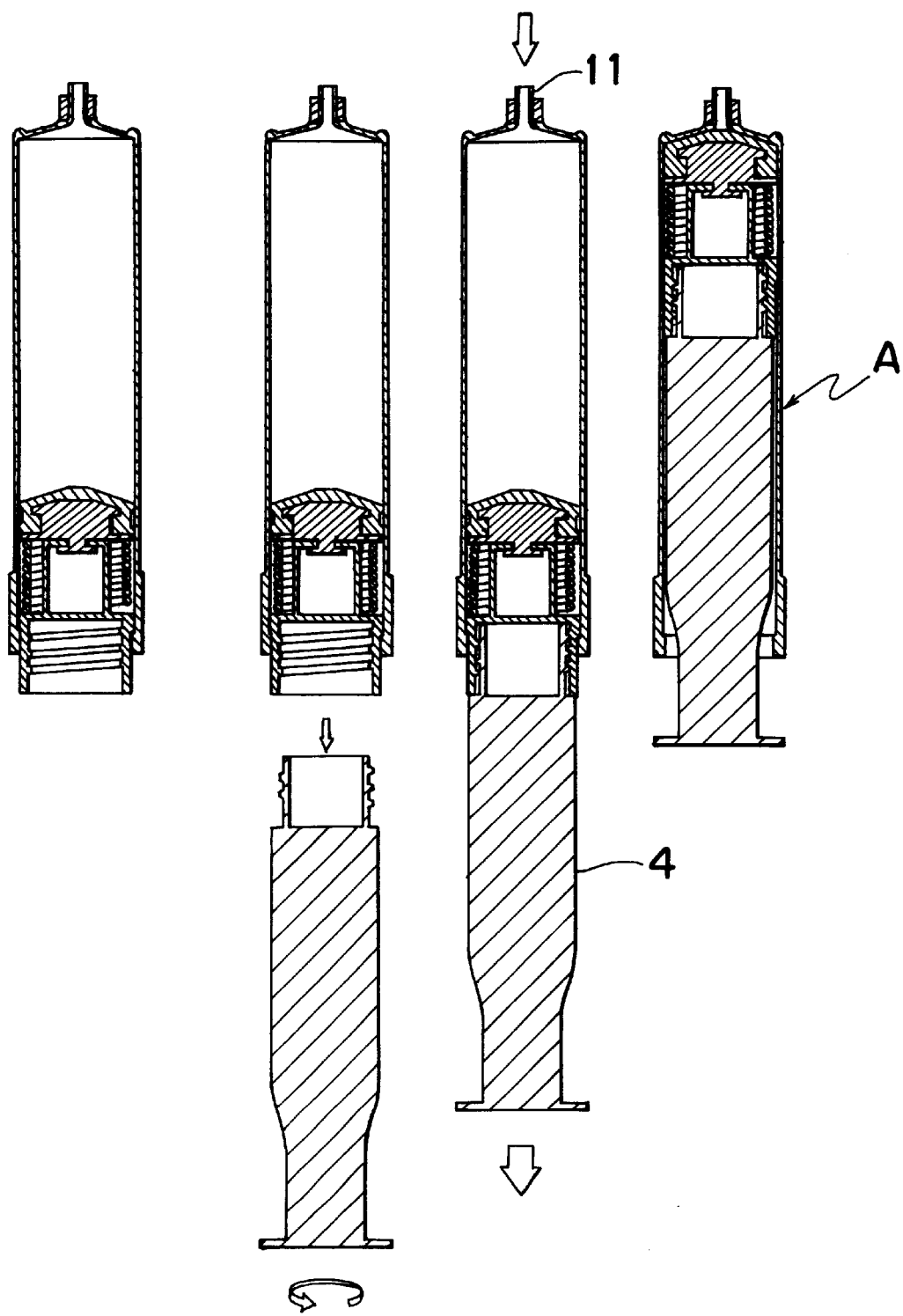
FIG. 9 is a schematic diagram of the delivery device of FIG. 1, illustrating steps of filling the delivery device with a drug solution.
Figure 11:
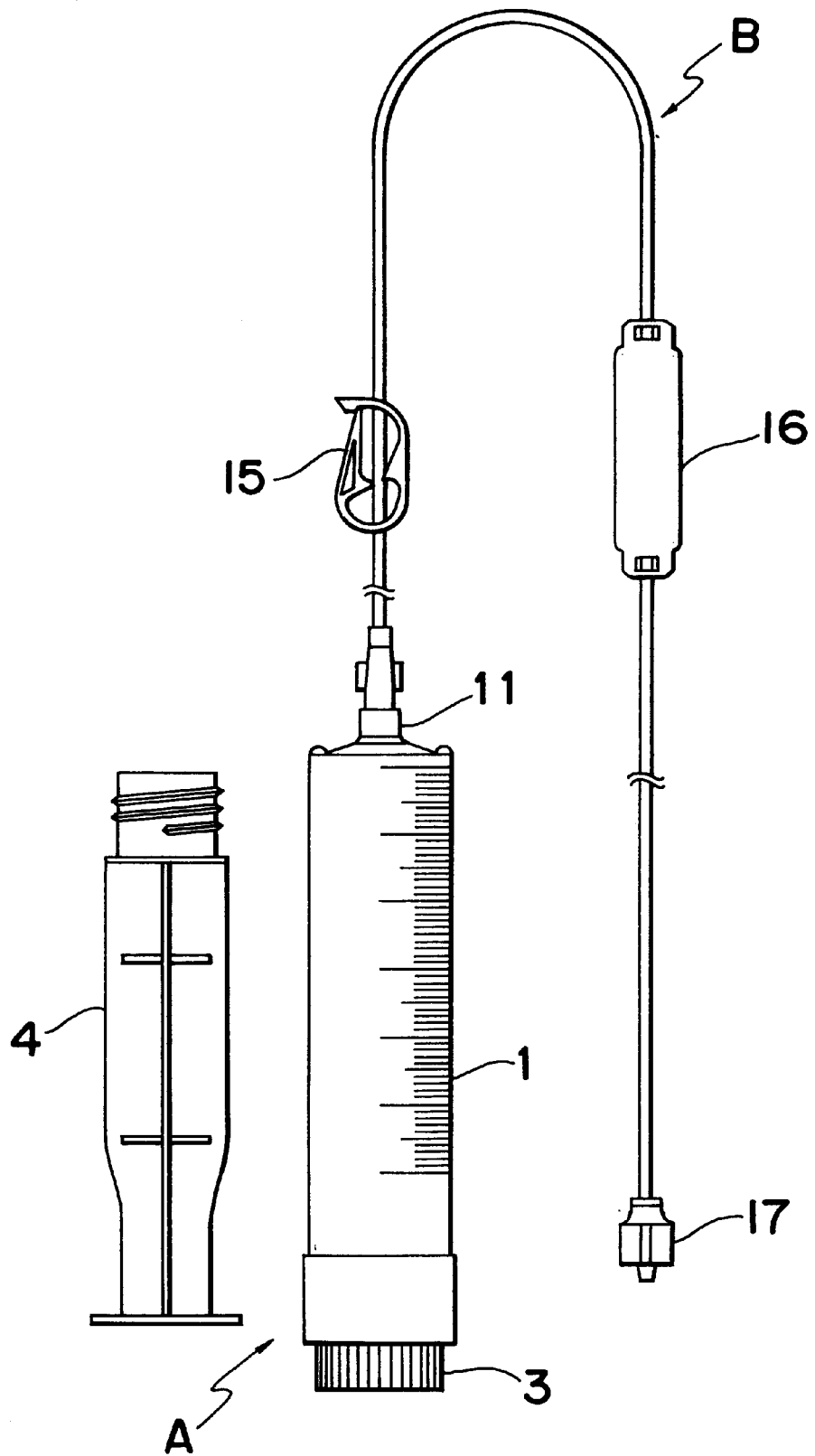
FIG. 11 is a side view of the delivery device of FIG. 1 with a tube provided with a flow control system connected thereto.

Use of the drug solution delivery devices will be explained below with reference to FIGS. 9–11.

The delivery device of FIG. 1 is originally lay in the state shown in FIG. 9(a). After connecting the port 11 of the barrel 1 to a drug container (not illustrated in the drawing), the plunger 4 is pulled toward the proximal end of the barrel 1 to fill the barrel 1 with a drug solution in the container as illustrated in FIG. 9(b). The plunger 4 is then removed from the connecting member 3 by rotating it around an axis thereof as illustrated in FIG. 9(c). At that time, the hook 21 of the gasket 2 is held under engagement with the connecting hole 331 of the connecting member 3 as illustrated in FIG. 10 (a). Under such a condition, the delivery device A is then connected at its port 11 to a tube B provided with a flow control system 16 as illustrated in FIG. 11. In FIG. 11, numeral 15 indicates a clamp in a closed condition, and numeral 17 indicates means for connection to a catheter (not illustrated in the drawings).

Then, the connecting member 3 is manually turned around an axis thereof as illustrated in FIG. 9(d) to orientate its connection hole 331 with the direction of the hook 21 of the gasket 2 as illustrated in FIG. 10(b), thereby releasing the gasket 2 from the connecting member 3. Under such conditions, the gasket 2 is begun to move forward by the restoring force of the spring 5 as shown in FIG. 10(c) as soon as the clamp 15 in FIG. 15 is removed from the tube B. Thus, the drug solution filled in the barrel 1 is delivered therefrom through the port 11.

As will be understood from the above description, the drug solution delivery device according to the present invention makes it possible to directly fill the barrel or syringe body with a drug solution only by simple operation of pulling the plunger. Thus, the operator is saved in work. Further, the barrel is formed into a syringe form, thus making it possible to observe a residual quantity of the drug solution in the barrel accurately.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A drug solution delivery device comprising:
    a barrel provided at a distal end thereof with a port and opened at a proximal end thereof;
    a gasket fluid-tightly and slidably arranged in a lumen of the barrel;
    a cylindrical connecting member having a proximal end and a distal end to which said gasket is being releasably connected, said connecting member being a stepped hollow cylindrical member having a small-sized cylindrical distal portion with an external diameter smaller than an internal diameter of the barrel, and wherein the spring is arranged round the distal portion;
    a plunger removably engaged with the proximal end of said connecting member; and
    a helical spring pressed and arranged between said gasket and said connecting member to push the gasket by a restoring force thereof to deliver a drug solution.

2. The drug solution delivery device according to claim 1, wherein the connection between said gasket and said connecting member is released by turning the connecting member around a central axis thereof.

3. The drug solution delivery device according to claim 2, wherein said connecting member is provided with one or more crossbars in a lumen of the distal portion thereof, and wherein said gasket is provided with a hook capable of being engaged with said crossbars.

4. The drug solution delivery device according to claim 3, wherein said connecting member is provided with a pair of crossbars symmetrically about an axis of the connecting member, and wherein said hook provided on said gasket is rotatably inserted into a gap between said crossbars in pair.

5. The drug solution delivery device according to claim 3, wherein said distal end of said connecting member is provided with a closure wall having a connecting hole on the central axis of said connecting member, and wherein said gasket is provided with a hook to be rotatably inserted into and releasably engaged with said connecting hole.

6. The drug solution delivery device according to claim 3, wherein said connecting member is provided in a side wall of the distal portion thereof with an L-shaped slit including an axial slit portion and a circumferential slit portion, and wherein said gasket is provided with means to be engaged with said circumferential slit portion.

7. The drug solution delivery device according to claim 1, wherein said distal end of said connecting member is provided with a closure wall having a circular connecting hole coaxial with the connecting member, and wherein said gasket is provided with at least one elongated flexible hook capable of being inserted into and engaged with the circular connecting hole, said gasket being adapted to be released from said connecting member by bending said hook inwardly.

8. The drug solution delivery device according to claim 7, wherein said gasket is provided with a pair of elongated flexible hooks symmetrically about an axis thereof.

9. The drug solution delivery device according to claim 1, wherein engagement between said plunger and said connecting member is released by rotating the plunger about an axis thereof.

10. A drug solution delivery device comprising:
    a barrel provided at a distal end thereof with a port and opened at a proximal end thereof;
    a gasket fluid-tightly and slidably arranged in a lumen of the barrel, said gasket being provided with at least one elongated flexible hook;
    a cylindrical connecting member having a proximal end and a distal end to which said gasket is being releasably connected;
    a plunger removably engaged with the proximal end of said connecting member; and
    a helical spring pressed and arranged between said gasket and said connecting member to push the gasket by a restoring force thereof to deliver a drug solution, said spring being arranged so as to surround a shank of said hook.

11. The drug solution delivery device according to claim 10, wherein said distal end of said connecting member is provided with a closure wall having a connecting hole coaxial with an axis of the connecting member, and wherein said hook is rotatably inserted into and engaged with said connecting hole.

12. The drug solution delivery device according to claim 11, wherein said connecting hole is circular and wherein said hook is flexible so that said gasket is released from the connecting member by inwardly bending the hook.

13. The drug solution delivery device according to claim 12, wherein said gasket is provided with a pair of hooks symmetrically about the axis thereof.

14. The drug solution delivery device according to claim 10, wherein said distal end of said connecting member is provided with one or two crossbars, which cross a lumen of the connecting member and are adapted to be engaged with said hook, and wherein said gasket is capable of being released from the connecting member by turning the connecting member around an axis thereof.

15. The drug solution delivery device according to claim 14, wherein said connecting member is provided at a distal portion thereof with a small-sized cylindrical portion having an external diameter smaller than the internal diameter of the barrel, and wherein said hook is arranged in the lumen of a protruded cylindrical portion along with the helical spring surrounding a shank of said hook.

16. The drug solution delivery device according to claim 15, wherein the inner surface of the barrel and the outer surface of the gasket are respectively provided with plural longitudinal ribs to prevent the gasket from being rotated around an axis thereof when rotating the plunger or the connecting member.

17. The drug solution delivery device according to claim 11, wherein said gasket is so designed as to be released by turning the connecting member about the axis thereof.

18. The drug solution delivery device according to claim 14, wherein said connecting member is provided with a pair of crossbars symmetrically arranged about an axis thereof, and wherein said hook is rotatably arranged between said pair of crossbars.

19. The drug solution delivery device according to claim 10, wherein engagement between said plunger and said connecting member is released by rotating the plunger about an axis thereof.

* * * * *